US010046099B2

(12) United States Patent
White et al.

(10) Patent No.: US 10,046,099 B2
(45) Date of Patent: *Aug. 14, 2018

(54) INTEGRATED WATER TESTING SYSTEM FOR ULTRA-LOW TOTAL CHLORINE DETECTION

(71) Applicants: Baxter International Inc., Deerfield, IL (US); Baxter Healthcare S.A., Glattpark (Opfikon) (CH)

(72) Inventors: Jeff White, Waukegan, IL (US); Ye Chen, Vernon Hills, IL (US); Yuanpang Samuel Ding, Libertyville, IL (US); Joel Titus, Lake Zurich, IL (US); Justin Rohde, Des Plaines, IL (US); Shincy Maliekkal, Glenview, IL (US); Kevin Cooper, Libertyville, IL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 226 days.

This patent is subject to a terminal disclaimer.

(21) Appl. No.: 14/865,583

(22) Filed: Sep. 25, 2015

(65) Prior Publication Data
US 2016/0030653 A1 Feb. 4, 2016

Related U.S. Application Data

(63) Continuation of application No. 13/797,086, filed on Mar. 12, 2013, now Pat. No. 9,162,021.
(Continued)

(51) Int. Cl.
*B01D 61/00* (2006.01)
*C02F 9/00* (2006.01)
(Continued)

(52) U.S. Cl.
CPC ........ *A61M 1/1656* (2013.01); *A61M 1/1603* (2014.02); *A61M 1/1664* (2014.02);
(Continued)

(58) Field of Classification Search
CPC ....... A61K 33/14; A61M 1/0209; A61M 1/16; A61M 1/1603; A61M 1/656;
(Continued)

(56) References Cited

U.S. PATENT DOCUMENTS 2,585,059 A 2/1952 Wallace
3,966,413 A 6/1976 Marinenko
(Continued)

FOREIGN PATENT DOCUMENTS

EP 1304559 4/2003
WO 96/25214 8/1996

OTHER PUBLICATIONS

Dimmock, et al. "Performance of the Orion 97-70 total residual chlorine electrode at low concentrations and its application to the analysis of cooling waters." Talanta 29, No. 7 (1982): 557-567.
(Continued)

*Primary Examiner* — Hayden Brewster
(74) *Attorney, Agent, or Firm* — K&L Gates LLP

(57) ABSTRACT

A system and method for determining a concentration of total chlorine in dialysis water are provided. The system comprises a main unit housing an iodide/water sample chamber and a reducing agent chamber. An electrode pair bridges the two chambers and generates tri-iodide proportional to the amount of total chlorine in the dialysis water. The electrode pair detects the amount of tri-iodide generated in proportion to the amount of active chloride in the dialysis water. The system is suitable for use in connection with, or for incorporation into, a water purification system for generating dialysis fluid, and may include a display that alerts
(Continued)

the user to stop or prevent a hemodialysis treatment if the total chlorine level exceeds a predetermined level.

10 Claims, 7 Drawing Sheets

Related U.S. Application Data

(60) Provisional application No. 61/716,970, filed on Oct. 22, 2012.

(51) Int. Cl.
```
A61M 1/16      (2006.01)
G01N 27/416    (2006.01)
G01N 33/00     (2006.01)
C02F 1/50      (2006.01)
G01N 27/30     (2006.01)
G01N 27/413    (2006.01)
B01D 35/00     (2006.01)
C02F 103/02    (2006.01)
```

(52) U.S. Cl.
CPC ............ *A61M 1/1668* (2014.02); *C02F 1/50* (2013.01); *G01N 27/30* (2013.01); *G01N 27/413* (2013.01); *G01N 27/4168* (2013.01); *G01N 33/0036* (2013.01); *A61M 2205/3327* (2013.01); *A61M 2205/502* (2013.01); *A61M 2205/75* (2013.01); *C02F 2103/026* (2013.01); *Y02W 10/33* (2015.05)

(58) Field of Classification Search
CPC ............ A61M 1/1656; A61M 1/3462; A61M 1/3643; A61M 1/001; A61M 2001/165; A61M 2001/1609; A61M 2001/1666; A61M 2001/3437; A61M 2205/3327; A61M 2205/502; A61M 2205/75; B01D 11/00; B01D 35/00; B01D 35/143; B01D 61/00; B01D 61/08; B01D 61/122; C02F 1/003; C02F 1/008; C02F 1/325; C02F 1/44; C02F 1/441; C02F 1/50; C02F 3/28; C02F 2103/26; C02F 2205/502; C02F 2205/3327; C02F 2209/29; G01N 21/00; G01N 21/05; G01N 21/78; G01N 21/253; G01N 21/314; G01N 21/552; G01N 21/553; G01N 21/8483; G01N 27/30; G01N 27/4168; G01N 27/413; G01N 31/22; G01N 33/00; G01N 33/0036; G01N 33/52; G01N 33/84; G01N 33/182; G01N 33/54373
USPC .................. 210/85, 96.2, 195.2, 646, 647
See application file for complete search history.

(56) References Cited

U.S. PATENT DOCUMENTS

| | | | |
|---|---|---|---|
| 4,049,382 | A | 9/1977 | Ross, Jr. et al. |
| 5,346,605 | A | 9/1994 | Wolcott et al. |
| 7,985,377 | B2 | 7/2011 | Vincent |
| 2008/0047846 | A1 | 2/2008 | Salzer |
| 2010/0051552 | A1 | 3/2010 | Rohde et al. |
| 2012/0103823 | A1 | 5/2012 | Dweik et al. |

OTHER PUBLICATIONS

Gottardi, et al. "Redox-iodometry: a new potentiometric method." Analytical and bioanalytical chemistry 382, No. 5 (2005): 1328-1338.

Hahn, et al. "Electrochemical investigation of chloramine T." Analytica chimica acta 289.1 (1994): 35-42.

Howe et al., "Microprocessor-controlled ion-selective-electrode determination of total chlorine." No. TVA/ONR/NRO-82/4; EPA-600/7-82-005. Tennessee Valley Authority, Chattanooga (USA). Office of Natural Resources; Environmental Protection Agency, Washington, DC (USA). Office of Environmental Processes and Effects Research, 1982.

IJspeerd, et al. "Biamperometric determination of free chlorine, hypochlorite, chlorite and chlorate in sodium chloride brine." Fresenius' Zeitschrift für analytische Chemie 288.5 (1977): 357-360.

International Search Report and Written Opinion for International Application No. PCT/US2013/065951 dated Jan. 31, 2014.

Len, et al. "Effects of storage conditions and pH on chlorine loss in electrolyzed oxidizing (EO) water." Journal of agricultural and food chemistry 50.1 (2002): 209-212.

Li, et al. "The determination of iodide based on a flow-injection coupling irreversible biamperometry." Chinese Chemical Letters 16, No. 12 (2005): 1629-1632.

Lichtig, et al. "Biamperometry in the Diffusion Current Region: Considerations for Its Application in Trace Analysis." 1993: vol. 4, No. 3.

Manns et al., The acu-men™: A new device for continuous renal replacement therapy in actue renal failure, Kidney International, 1998, pp. 268-74, vol. 54.

Marks, et al. "Amperometric Methods in Control of Water Chlorination." Analytical Chemistry 19.3 (1947): 200-204.

Nascimento, et al. "Automatic determination of chlorine without standard solutions using a biamperometric flow-batch analysis system." Talanta 81.1 (2010): 609-613.

Ohura, et al. "Simultaneous potentiometric determination of ClO3—ClO2-and ClO3—HClO by flow injection analysis using Fe (III)-Fe (II) potential buffer." Talanta 49, No. 5 (1999): 1003-1015.

Oliveira, et al. "A coulometric flow cell for in-line generation of reagent, titrant or standard solutions." Microchemical journal 82.2 (2006): 220-225.

Rigdon, et al. "Determination of residual chlorine in water with computer automation and residual-chlorine electrode." Analytical Chemistry 50, No. 3 (1978): 465-469.

Saad, et al. "Sequential flow injection determination of chlorine species using a triiodide-selective electrode detector." Analytical sciences 22.1 (2006): 45-50.

Seymour, et al. "Reaction with N, N-Diethyl-p-phenylenediamine: A Procedure for the Sensitive Square-Wave Voltammetric Detection of Chlorine." Electroanalysis 15, No. 8 (2003): 689-694.

Tougas, et al. "Theoretical and experimental response of a biamperometric detector for flow injection analysis." Analytical Chemistry 57, No. 7 (1985): 1377-1381.

Whitney, et al. "Solubility of chlorine in water." Industrial & Engineering Chemistry 33, No. 6 (1941): 741-744.

Combined Search and Examination Report Under Sections 17 and 18(3) issued in related GB Patent Application No. 1713538.5 dated Sep. 25, 2017.

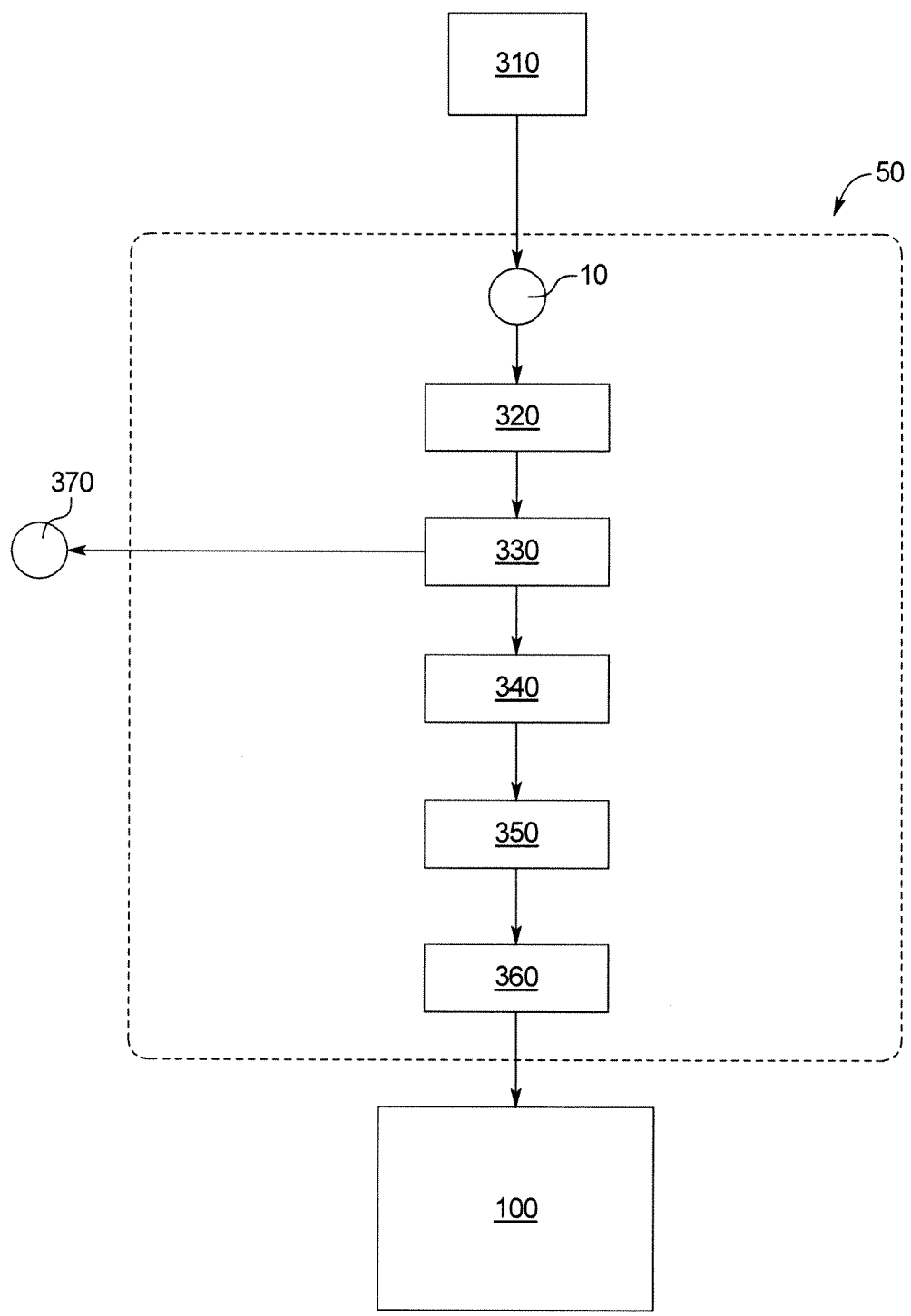

INTEGRATED WATER TESTING SYSTEM FOR ULTRA-LOW TOTAL CHLORINE DETECTION

PRIORITY CLAIM

This application is a continuation of U.S. patent application Ser. No. 13/797,086, filed on Mar. 12, 2013, now U.S. Pat. No. 9,162,021, which claims priority to U.S. provisional patent application Ser. No. 61/716,970, filed on Oct. 22, 2012, the entire contents of each of which are incorporated herein by reference and relied upon.

BACKGROUND

This application relates generally to water purity qualitative analysis, and in particular to water used for medical applications.

Water purity qualitative analysis determines the presence or absence and the amounts of chemicals and their mixtures in water. Water purity qualitative analysis can require field kits for testing the water facilities. The field test kits are known in general to have disadvantages including inaccuracies in data, false positives, limitations of single-factor testing, e.g., in measuring chlorine levels in pools and spas, and overall accuracy. Disadvantages of field qualitative testing kits also include an inability to reproduce statistics. Outdoor and indoor conditions, such as humidity, temperature, wind, rain and noise add to the inherent disadvantages of test kit qualitative field-type water monitoring.

Testing can alternatively be done by mixing water with powders in vials. Both strips and vials change the color of water to indicate if the water purity meets safe levels. Color change analysis leaves open the possibility that the person viewing the change cannot see color well and that multiple viewers may compare the water color to the test markers differently. Color viewing test results accordingly provide low to moderate accuracy in measuring amounts of chlorine, bacteria and acidity (pH levels), which each affect water purity.

Sensors are used in municipal, industrial and residential water systems to test variables affecting water purity for human consumption and use, as well as to monitor water purity for healthy ecosystems of other living organisms. Sensors measure temperature, pH levels and desalination (salt control) compounds. However, using sensors in qualitative water purity field testing can result in drawbacks due to moderate measurement accuracy for multiple types of water purity statistics.

Using chemistry-based field-testing to gather qualitative water-purity data gives incomplete statistical outcomes, similar to the pH colorimetric qualitative testing. Operating at a neutral pH, chemistry-based testing, like colorimetric testing, measures particular aspects of inorganic substances in water, rather than all its characteristics. As an example, at neutral pH, both of the chemistry-based and colorimetric tests measure dissolved iron amounts, but not iron particles. In addition, ammonia levels from biological decay compromise qualitative measurements using chemistry-based field testing of nutrients in wastewater.

As discussed above, known water testing techniques have multiple drawbacks. In a medical setting in which the testing techniques are relied upon, for example before allowing a therapy to take place, the ramifications associated with inaccurate testing can be serious. If the water testing underreports the level of a certain substance in the tested water, the water can be allowed to be used when it should not be, resulting in a potentially unsafe condition for the patient or in the malfunctioning of a machine running a medical treatment for the patient. The reverse situation is also problematic. If the testing is oversensitive, or in any case gives false positive or overreported results, the system may needlessly alarm or erroneously prevent a treatment from occurring.

Another problem with the above testing is its manual nature. Even if the testing assay is otherwise sound, the patient or caregiver can introduce error. And even if the testing and the operator performance are sound, manual testing still requires extra steps, adding time, complexity and cost.

An improved water quality system and method are needed accordingly.

SUMMARY

The present disclosure relates to water testing and in particular to the testing of total chlorine (e.g., free chlorine and other similar bound active chlorine species commonly known as chloramines) in water. One application for the testing apparatus and methodology of the present disclosure is to make water for use with online hemodialysis. Online hemodialysis makes dialysate from purified water. The purified water can be made from house tap water. In a hospital or clinic, the house tap water is the water found for example at sinks and drinking fountains in the hospital or clinic. At home, the tap water is the patient's home tap water.

Making dialysate from purified tap water involves adding salts to the purified water. The goal is to achieve the electrolyte status of blood plasma, or the water component of blood. Because hemodialysis works on the principles of osmosis, diffusion and equilibration, the treatment needs to use a treatment fluid, or dialysate, that has the chemical composition of purified blood. There are many components to the patient's blood that are healthy and needed and should not be removed during treatment. Red and white blood cells and platelets are examples. But these healthy and needed components are retained mechanically by making the pores in the dialyzer membranes too small for the cells and the platelets to pass through from the patient or blood side of the dialyzer to the treatment or dialysate side of the dialyzer.

Salts or electrolytes such as a potassium, calcium, sodium and magnesium are also, at least to a certain extent, healthy and needed components of blood. But salts are dissolved in the blood water or plasma. Thus if pure water were to be run as treatment fluid instead of dialysate, the large osmotic or diffusive gradient would pull too much of the salt from the blood and create a highly unsafe condition for the patient. For that reason, great care is taken in the online manufacture of dialysate from purified water to ensure that a desired amount of salt is present in the dialysate before the dialysate is allowed to be delivered to the dialyzer and osmotically or diffusively comingle with the patient's blood.

One method for ensuring that a desired amount of salt is present in the dialysate is through the use of conductivity sensors. Adding salt to the purified water generally increases electrical conductivity sensed by the sensors. The desired amount of salt will have a specific conductivity. The online machine mixes pure water and salts from concentrate containers until the desired conductivity is sensed, after which the dialysate can be delivered to the dialyzer.

The online hemodialysis system contemplated for use with the present apparatus and methodology employs a water purification system that removes preexisting salts, such as chlorine, from the incoming tap water so that the dialysate generation portion of the system can begin with salt-less, zero-conductivity water to which desired, blood-friendly salts are added. Also, free chlorine in dialysate can cross the dialysis membrane and destroy the patient's red blood cells. Free chlorine in solution can also generate chloramines, which are known to induce hemolytic anemia. The useful lifetime of dialysis membranes is also shortened when free chlorine is present in dialysate. For at least these reasons, AAMI/ANSI recommends that dialysate contain less than 0.5 mg/L of free chlorine.

The present system and apparatus provide a way to automatically and precisely detect either (i) the incoming total chlorine level of the tap water or (ii) the total chlorine level present after the tap water has flowed through a filter included to remove impurities such as active chlorine compounds (e.g., a filter check). The apparatus and method do not require input from the patient or caregiver. The apparatus and method are also accurate, so that the system alarms or otherwise responds when chlorine levels are too high but greatly reduces the amount of false trippings and needless treatment shutdowns.

In an embodiment, the system and corresponding method include a main testing unit in fluid communication with an iodide reservoir and a reducing agent reservoir. The iodide reservoir contains an iodide donor or a mixture of iodide donors, such as potassium iodide ("KI") and/or sodium iodide ("NaI"). The reducing agent reservoir contains a spontaneous electron acceptor (e.g., a reducing agent) or a mixture of spontaneous electron acceptors such as sodium sulfate ("$Na_2SO_4$"). A membrane, such as a hydrophobic membrane, is provided with and divides the main unit into a reducing agent chamber and an iodide and sample chamber, which are in fluid communication with the reducing agent reservoir and the iodide reservoir, respectively. The main testing unit further includes an electrode pair capable of both generating tri-iodide and determining a resulting tri-iodide concentration. In one implementation, one electrode of the pair is in contact with fluid in the reducing agent chamber and the other electrode of the pair is in contact with fluid in the iodide and sample chamber. In some embodiments, the iodide and sample chamber is a tube disposed within the reducing agent chamber, which can in turn be a larger diameter tube. In some embodiments, the iodide and water sample chamber is in fluid communication with the reducing agent chamber via microchannels, for example in a cassette.

In an embodiment, water quality is tested by determining a level of total chlorine. In such an embodiment, a water sample is provided to the iodide and sample chamber of the main testing unit, which is in fluid communication with the iodide reservoir, and is separated by the membrane from the reducing agent chamber, which is in turn in fluid communication with the reducing agent reservoir. Once the water sample is pumped to the iodide and sample chamber, a baseline is measured. Then a voltage is applied to the electrode pair. The voltage produces tri-iodide. This production of tri-iodide causes current to flow through the electrodes which, after a suitable relaxation period, is measured via the electrode pair.

In an embodiment, the concentration of total chlorine in water under test is determined by measuring an initial, baseline current associated with any tri-iodide that may already be in the system (e.g., without generating any tri-iodide or adding external tri-iodide), followed by repeated cycles of (a) generating tri-iodide by application of current to the electrode pair and (b) measuring the resulting voltage in the same electrode pair, typically after a suitable relaxation period. In an embodiment, the voltage is measured and converted to a current measurement using Ohm's law. The plurality of voltage measurements (or calculated current measurements) are plotted against relative or absolute tri-iodide concentration. In this way, a calibration curve including a baseline, the test measurement, and several additional data points of known iodide concentration increases is created. The amount of total chlorine present in the water under test is proportional to the difference in tri-iodide concentrations from subsequent cycles as described above.

In some embodiments, the concentration of total chlorine in the water under test is determined from (a) a background voltage or current measurement, (b) a baseline voltage or current measurement, and (c) from one to about twenty cycles of (i) generating tri-iodide by application of current to the electrode pair and (ii) measuring the resulting voltage in the same electrode pair after a suitable relaxation time. The choice of the number of cycles in step (c) will reflect a balance between accuracy of the total chlorine determination and the amount of time required to perform the analysis. More cycles generally lead to more accurate results. However, each cycle can take from several seconds to several minutes depending on operating parameters, and thus in the interest of providing efficient and safe dialysis, the fewest number of cycles in step (c) required to provide an accurate total chlorine determination is desired in one embodiment. Thus, in some embodiments, step (c) includes one to five cycles. In some embodiments, a first determination of total chlorine includes a larger number of cycles in step (c), while subsequent determinations of total chlorine include fewer cycles in step (c). For example and without limitation, a first determination of total chlorine in water under test includes three, four or five cycles in step (c). A subsequent or a plurality of subsequent total chlorine determinations then includes one, two or three cycles in step (c).

It is accordingly an advantage that the water purification system and method of the present disclosure is performed automatically.

It is another advantage that the water purification testing system and method of the present disclosure is calibrated automatically.

It is a further advantage that the water purification testing system and method of the present disclosure is cleaned automatically.

It is yet another advantage that the water purification testing system and method of the present disclosure is accurate.

It is yet a further advantage that the water purification testing system and method of the present disclosure is low cost.

It is still another advantage that the water purification testing system and method of the present disclosure is built into or packaged with a water purification system.

It is yet a further advantage that the water purification testing system and method of the present disclosure requires minimal maintenance.

Still another advantage is that the disclosure is to provide a water purification testing apparatus and method that reduces user interaction.

Still a further advantage is that the water purification testing system and method of the present disclosure outputs electrically for system integration.

Additional features and advantages are described herein, and will be apparent from, the following Detailed Description and the figures.

BRIEF DESCRIPTION OF THE FIGURES

FIG. 7 is a schematic view of one embodiment of a water treatment system which includes a detection cell of the present disclosure.

DETAILED DESCRIPTION

Figure 1:
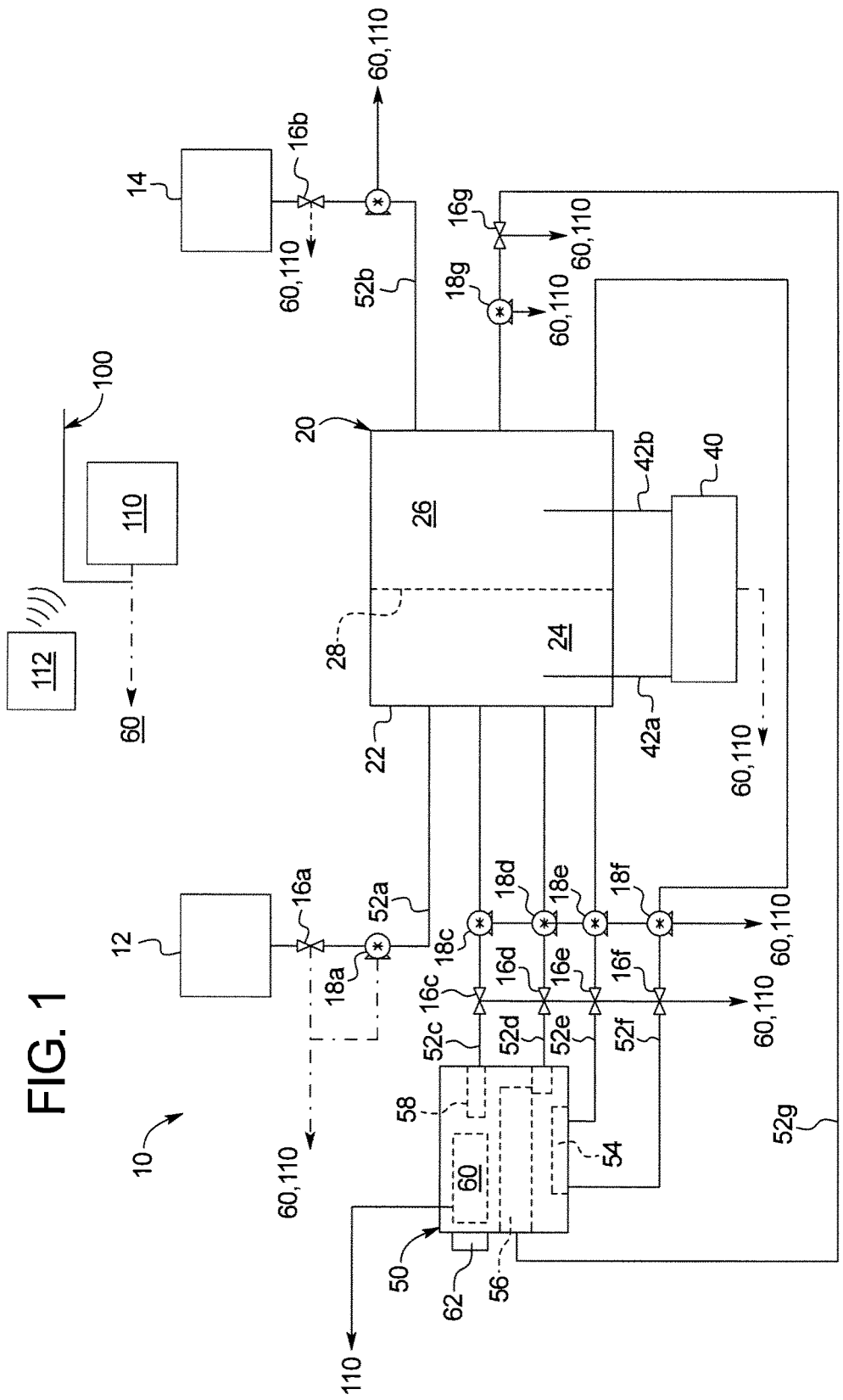
FIG. 1 is a schematic view of one embodiment of a water purification testing system and method of the present disclosure.

As discussed above, a more accurate and easier to use total chlorine sensor is needed to minimize the occurrences of false positives or trips inherent with other chlorine testing methods (e.g., testing strips). False positive results are problematic in the purification of water for hemodialysis because they force users to stop treatment and perform maintenance. False negatives may result in an unsafe treatment being performed. The testing system and method discussed herein greatly reduces the false tripping, can detect at least as low as 0.05 parts per million ("ppm") total chlorine concentration in one implementation, provides an automatic detection function (including calibration), built-in packaging, and the ability to be implemented with a relatively small incremental cost. In other embodiments, the testing system and method is capable of detecting 0.01 ppm total chlorine.

As used herein, the term, "total chlorine" refers to any and all reactive chlorine compounds including, but not limited to, chlorine gas (e.g., dissolved chlorine gas), hypochlorite, chloramines, and chloramine-T. Total chlorine may but does not have to exclude chloride ions (e.g., metal chlorides such as sodium chloride, potassium chloride, etc.).

In one embodiment, the water purity testing apparatus and associated methodology are integrated into a water purification machine, such as one set forth in U.S. Patent Publication No. 2011/0197971, entitled, "Water Purification System And Method", filed Apr. 25, 2011, which is in turn used with an online hemodialysis machine, such as one set forth in U.S. Patent Publication No. 2009/0101549, entitled, "Modular Assembly For A Hemodialysis System", filed Aug. 27, 2008, the entire contents of each of which are incorporated herein by reference and relied upon. The electrical and/or computer control units discussed below may be located in the water purification machine and/or the dialysis machine. The pumps and valves discussed below are located in one embodiment within the water purification machine. Thus, there can be electrical cabling running from the dialysis machine to the water purification machine to control the pumps and valves located within the water purification machine. Alternatively, the water purification machine can also house its own electrical and/or computer control unit for controlling the purification units pumps and valves. Even here, however, the water purification control unit can communicate wired or wirelessly with the dialysis machine and be subordinate, for example, to the dialysis machine's master controller, e.g., sending chlorine data to same. Either one or both of the control units of the dialysis unit or the water purification unit could then place the overall system into an alarm state if needed.

In one embodiment, the system and method of the present disclosure measure chlorine indirectly by allowing the molecule to oxidize iodide to tri-iodide and measuring the corresponding voltage change. Total chlorine may be introduced into the system through many forms including, but not limited to, chlorine standard free chlorine (e.g., $Cl_2$ dissolved in water), hypochlorite (e.g., as bleach), or chloramine-T. In a preferred embodiment, chloramine-T is used as a stabilized form of total chlorine and is added to an iodide-containing reagent solution. Chloramine-T degrades to hypochlorite and hypochlorite in turn reacts with iodide via the following relationship to form tri-iodide:

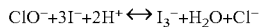

$$ClO^- + 3I^- + 2H^+ \leftrightarrow I_3^- + H_2O + Cl^-$$

Calibration of the electrode system is achieved by electrochemically generating tri-iodide and measuring the system response (voltage). Tri-iodide may be generated in multiple sessions to improve the estimation of the dependence of voltage with changes in tri-iodide concentration. The amount of tri-iodide generated is computed from measured current moving though the electrode placed into a potassium iodide chamber. The current, in turn, is determined by measuring the voltage change across a resistor of known value. Tri-iodide generation can be accomplished using metals including, but not limited to, platinum and stainless steel, and by using $SO_4^{-2}$ as an auxiliary electrolyte. In this scenario, the electrochemical equations governing the generation of tri-iodide are:

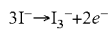

$$3I^- \rightarrow I_3^- + 2e^-$$

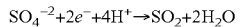

$$SO_4^{-2} + 2e^- + 4H^+ \rightarrow SO_2 + 2H_2O$$

In one preferred embodiment, sulfate ions are introduced through sodium sulfate and iodide ions are introduced as potassium iodide. Sodium sulfate concentrations and potassium iodide concentrations above 5 g/L have been seen to yield reproducible generations of tri-iodide molecules. Also in a preferred embodiment, the generation voltage is maintained by a voltage source set to deliver 700 mV. The corresponding generating voltage ranges from 0.5 to 3.5 V and depends on the concentration of iodide and sulfate ions.

Referring now to the drawings and in particular to FIG. 1, in one embodiment an, e.g. embedded, testing system 10 provides two reagent reservoirs including a iodide reservoir or cell 12 and a reducing agent reservoir or cell 14. Iodide reservoir or cell 12 includes an iodide source. Any iodide source may be used, provided that the iodide source completely dissociates in water. Non-limiting examples of iodide sources include alkaline iodide reagents such as potassium iodide (KI) and/or sodium iodide (NaI). Reducing agent reservoir or cell 14 includes a reducing agent. Any suitable reducing agent may be used, provided that the reducing agent readily accepts electrons. One non-limiting example of a reducing agent is an alkaline sulfate such as sodium sulfate ($Na_2SO_4$). In one embodiment, iodide reservoir or cell 12 includes potassium iodide and reducing agent reservoir or cell 14 includes sodium sulfate. System 10 also includes a main testing unit 20 that operates with two electrical control circuits 30 and 40. Main testing unit 20 includes a liquid-tight housing 22, which is separated into two compartments 24 and 26 by a semi-permeable membrane 28 to allow charged ions to pass through the membrane, preventing an open circuit. Housing 22 can be metal or plastic as desired. Compartments 24 and 26 can be opened or closed and sized to be the same or to have different volumes as desired. Membrane 28 can be a semipermeable membrane with a molecular weight cut-off ("MWCO") of less than 1,000 Daltons, in one preferred embodiment less than 500 Daltons, and in another preferred embodiment from about 100 Daltons to about 500 Daltons. In some embodiments, membrane 28 is made of a material including one or more of: a polyether sulfone, a cellulose, and/or a nylon. In one embodiment, membrane 28 is an Ultracel PL-1 from Millipore (MWCO 1000). In some embodiments, the membrane allows only positive charge to penetrate. In some embodiments, the membrane allows only negative charges to penetrate. In some embodiments, the membrane allows both positive and negative charges to penetrate.

Reagent reservoirs 12 and 14 are both in valved and pump communication with main testing unit 20. In an embodiment, the iodide reservoir 12 and/or the reducing agent reservoir 14 are provided in a cartridge or cassette form. In an embodiment, the cartridge includes iodide reservoir 12 and reducing agent reservoir 14. In another embodiment, the cartridge or cassette includes iodide reservoir 12, reducing agent reservoir 14, and electrodes 42a and 42b for circuitry 40. In an embodiment, the iodide is provided in a liquid form such as a pre-mixed solution or a concentrate, or in a solid form such as a crystal, a powder, and/or a tablet. In some embodiments, the iodide reservoir includes potassium iodide. In an embodiment, the reducing agent is provided in a liquid form such as a pre-mixed solution or a concentrate, or in a solid form such as a crystal, a powder, and/or a tablet. In some embodiments, the reducing agent reservoir includes sodium sulfate. When either reagent is provided in dry form, the associated control unit can control the associated pumps and valves to first pump water into the crystal, dry powder or tablet containers for mixing before pumping liquid iodide reagent or reducing agent from the containers.

In the embodiment illustrated in FIG. 1, the iodide cell or reservoir 12 communicates fluidly with the iodide reagent and sample chamber or compartment 24 of main testing unit 20 via line 52a including a valve 16a and pump 18a. Reducing agent cell or reservoir 14 in turn communicates fluidly with chamber or compartment 26 of main testing unit 20 via line 52b including valve 16b and pump 18b.

FIG. 1 also illustrates that the main testing unit 20 is fluidly connected to a water purification unit or machine 50, which can be the water purification machine described above in the incorporated U.S. 2011/0197971 Publication. In the illustrated embodiment, there are multiple fluid connections between water purification machine 50 and main testing unit 20. In particular, test water is pumped from a test water outlet or supply 58 of water purification machine 50 to iodide and sample chamber or compartment 24 of main testing unit 20 via line 52c, including valve 16c and pump 18c. Deionized ("DI") water is pumped from DI water outlet or supply 56 of water purification machine 50 to iodide and sample compartment 24 of main testing unit via line 52d, including valve 16d and pump 18d. Drainage water is pumped from the iodide and sample compartment 24 of main testing unit 20 to a drain 54 of water purification machine 50 via line 52e, including valve 16e and pump 18e.

Drainage water is also pumped from reducing agent chamber or compartment 26 of main testing unit 20 to drain 54 of water purification machine 50 via line 52f, including valve 16f and pump 18f. DI water is also pumped from DI water outlet or supply 56 of water purification machine to reducing agent compartment 26 of the main testing unit via line 52g, including valve 16g and pump 18g.

In an alternative embodiment, a single drain pump (18e or 18f) is used instead of the separate drain pumps illustrated and drain valves 16e and 16f are sequenced to selectively drain from one or both of chambers or compartments 24 and 26. Alternatively or additionally, a single DI pump (18d or 18g) is used instead of the multiple DI pumps illustrated and DI valves 16d and 16g are sequenced to selectively pump DI water to one or both of chambers or compartments 24 and 26. Thus, the number of pumps shown in FIG. 1 can be reduced by at least two pumps from the number of pumps illustrated.

As described in further detail below, chlorine testing is performed using the valves and pumps provided or operable with lines 52a to 52c in association with the circuit 40 and electrode pair 42a and 42b. Calibration is performed using the valves and pumps provided or operable with lines 52a, 52b, 52d and 52g in association with circuit 40 and electrodes 42a and 42b. Rinse is performed using the valves and pumps provided or operable with lines 52d to 52g.

Determination of the total chlorine content of the water test sample is sensitive to the volume of the water test sample provided. Accordingly, in an embodiment, the amount of test sample water is accurately metered and/or pumped into main test unit 20 by, for example, a microfluidic pump. One suitable microfluidic pump is a SmoothFlow™ pump provided by Microfluidica, LLC (Glendale, Wis.). Although any amount of water under test may be used, typically a small volume, for example from about 50 µL anywhere to about 500 µL of water under test are pumped into main testing unit 20.

In an embodiment, pumps 18a to 18g are electrically operated pumps, such as microfluidic pumps, and can be gear, centrifugal, piston or vane pumps. The pumps may have liquid contacting surfaces that are made of medical grade plastic or stainless steel, such that the surfaces cannot themselves corrode or contaminate water, such as test, DI or drain water, running past the surfaces, or they may have liquid contacting surfaces that may contaminate the fluid if placed in the drain line. In an alternative embodiment, pumps 18a to 18g are small peristaltic (roller or linear) or tube actuating (e.g., shuttle) pumps that pump water, such as test, DI or drain water, through a respective tube by collapsing, squeezing and/or crushing the tube sequentially to move the fluid. In another alternative embodiment, pumps 18a to 18g are electrically and/or pneumatically actuated membrane pumps that move water, such as test, DI or drain water, by fluctuating a membrane back and forth between a chamber of known volume. Pumps 18a to 18g can further alternatively be any combination of the above types of liquid pumps, selected to optimize performance, cost and reliability.

It should be appreciated from the above discussion of the various types of pumps 18a to 18g, that lines 52a to 52g can be made of different materials, such as stainless steel or plastic. Suitable plastics include polyvinylchloride ("PVC"), for example, when lines 52a to 52g do not have to be deformed for, e.g., peristaltic or shuttle pumping, or silicone, for example, when lines 52a to 52g are deformed for, e.g., peristaltic or shuttle pumping. If membrane pumps are used, lines 52a to 52g may contain sections that transition to a chamber having membrane sheeting, which can likewise be plastic, such as PVC sheeting.

Each of valves 16a to 16g can be an electrically or pneumatically actuated valve. In an embodiment, valves 16a to 16g include a valve housing to which the respective line 52a to 52g is sealingly attached. Here, each line 52a to 52g can be broken and sealingly attached to inlet and outlet connectors of the respective valve 16a to 16g. Also here, the valve includes its own internal opening/shutting mechanism. Alternatively, valves 16a to 16g are electrically or pneumatically actuated solenoid valves that operate directly on lines or tube 52a to 52g, e.g., compressible plastic tubes. The solenoid valves can for example be fail-safe or spring-operated closed and electrically or pneumatically actuated open. In a further alternative embodiment, valves 16a to 16g are electrically and/or pneumatically actuated membrane valves, for example, provided as part of a disposable cassette that includes a hard, valve chamber part that is sealed fluidly by one or more flexible, e.g., PVC, sheet that is flexed to close and open the hard part of the chambers. Here, the hard part can also be formed with pump chambers and the same one or more flexible sheet can be used for pumps 18a to 18g. Valves 16a to 16g can further alternatively be any combination of the above types of liquid valves, selected to optimize performance, cost and reliability.

System 10 includes a control unit 60, which in the illustrated embodiment is housed inside water purification machine 50. Control unit 60 can include one or more processor, one or more memory and one or more control circuitry, such as control circuit 40. Pumps 18a to 18g and valves 16a to 16g can be operated under the control of a computer program stored at control unit 60. Control unit 60 is in one embodiment the same control unit 60 used for all of water purification machine 50. Hence, control unit 60 may include a master processor that communicates (i) with a user interface 62 of water purification machine 50, (ii) with a wired or wireless data link to a corresponding control unit 110 of dialysis machine 100 that uses water produced by water purification machine 50, and (iii) with one or more delegate processor that runs the electrical equipment provided within water purification machine 50, including pumps 18a to 18g and valves 16a to 16g. Either one or both of the master and delegate processors of control unit 60 may receive signal inputs from and send signal outputs to control circuit 40.

In one embodiment, the master processor sends output data, such as chlorine content output data, to one or both of a user interface of water purification machine 50 and/or to the control unit 110 of the dialysis machine 100. It is contemplated for dialysis machine 100 to sit on top of water purification machine 50. Thus, either user interface 62 of water purification machine 50 and/or user interface 112 of dialysis machine 110 could be used to inform the patient or caregiver of the chlorine results and to communicate any associated alerts or alarms. In one embodiment, however, main user interface 112 of dialysis machine 110 is a wireless, e.g., tablet, user interface that allows the patient or caregiver to reside remotely from the dialysis machine while still viewing information concerning same. Here, it is desirable to send water purification machine 50 data, such as chlorine content data, via control unit 60 to control unit 110 of dialysis machine 100, which in turn forwards the pertinent data to remote user interface or tablet 112.

In an alternative embodiment, the generation and receipt of signals to and from control circuit 40 and the control of pumps 18a to 18g, valves 16a to 16g and possibly other electrical components of water purification machine 50 is done via control unit 110 of the dialysis machine 100. Here again, control unit 110 of dialysis machine 100 can forward pertinent data to the remote user interface or tablet 112 of dialysis machine 100. When control unit 110 of machine 100 is the primary control unit for water purification system 10, control unit 60 may be eliminated, at least as far as system 10 is concerned, or limited to a smaller number of tasks.

In any case, control unit 60 and/or control unit 110 opens valves 16a to 16g and operates pumps 18a to 18g to meter into chambers or compartments 24 and 26 precise amounts of desired fluids, e.g., DI water, iodide solution, reducing agent solution or test water solution, or to remove precise amounts of fluids from chambers or compartments 24 and 26 to drain 54. The metering can be run open loop and rely on the accuracy of the pumping mechanism to deliver the correct ratio of fluids. Alternatively or additionally, feedback in the form of conductivity sensing may be used to ensure that the proper proportioning of fluids takes place within chambers or compartments 24 and 26.

As illustrated, in an embodiment, main unit 20 is placed in fluid communication with deionized water via outlet or storage 56 from water purification unit 50. Deionized water is pumped into the main unit (e.g., into the chambers or the compartments 24 and 26 separately) to flush the water test sample and any residual tri-iodide and/or total chlorine from the main unit. In some embodiments, the total chlorine level is determined before and/or during each dialysis treatment. Here, an aliquot of water from water purification unit 50 for making dialysate is diverted to system 10 and analyzed by the methods disclosed herein before any water from purification unit 50 is allowed to be used to make dialysate at machine 100. Control unit 60 or 110 can be programmed to prevent and/or suspend dialysis fluid preparation when the total chlorine level in the dialysis water exceeds a threshold level, for example 0.1 ppm. In some embodiments, water from purification unit 50 is analyzed after a dialysis treatment is completed, such that corrective action can be taken to reduce total chlorine levels in the water before a subsequent dialysis treatment is required, and providing typically at least twenty-four hours before the subsequent treatment.

As discussed above, system 10 can be implemented within water purification unit 50. If so, main unit 20 can be positioned downstream of one or more filter used in water purification unit as specified in the U.S. 2011/0157971 Publication. For example and without limitation, main unit 20 may be in fluid communication with a carbon filter, wherein water exiting the carbon filter, or samples thereof, is then tested for total chlorine compounds according to the present disclosure. A failed test likely means that the carbon filter is faulty or spent and needs replacement. A suitable message can then be displayed, e.g., on user interface 112 of dialysis machine 100.

Electrical circuit 40 operates via electrodes 42a and 42b to perform both calibration and total chlorine sensing. Electrode 42a is inserted into iodide and sample compartment 24, while electrode 42b is inserted into reducing agent chamber or compartment 26. Electrodes 42a and 42b can be metallic. In some embodiments, electrodes 42a and 42b are each provided with or are in electrical communication with a resistor (e.g., a 1 k$\Omega$ to 5 k$\Omega$ resistor). As described above, the iodide solution and the reducing agent solution are separated by membrane 28, which permits electricity but not fluid to flow across the membrane. In one embodiment, membrane 28 includes micropores or perforations in the membrane, which are formed such that there are about three (3) to about twenty (20) holes, each hole sized such that charge can freely pass between the chambers without any fluid passing between the chambers. In one example embodiment, the membrane is formed of a silicone elastomeric material and includes about seven micropores formed by a 28-gauge needle. The elastomeric nature of the membrane causes the holes to substantially close, allowing electrical charge to pass through without permitting fluid to pass between the chambers. One suitable membrane 28 is made of silicone tubing. Another suitable membrane 28 is provided by Millipore and is sold under the trade name ULTRACEL PL-1. When a voltage is applied to electrical circuit 40 (e.g., about 1 volt DC), the induced current generates tri-iodide from the iodide solution.

Electrical circuit 40 also detects the amount of tri-iodide generated at the first electrical control circuit. Here, electrical control circuit 40 is a tri-iodide detection circuit in which electrodes 42a and 42b can be, e.g., platinum, stainless steel, gold, or combinations or alloys thereof. When a low voltage is applied across electrodes 42a and 42b, the induced current can be measured and used as a proxy for the amount of tri-iodide in the solution, and therefore the amount of total chlorine in the water sample. In some embodiments, the system is capable of determining an amount of total chlorine in the water sample as low as about 0.05 ppm.

Figure 2:
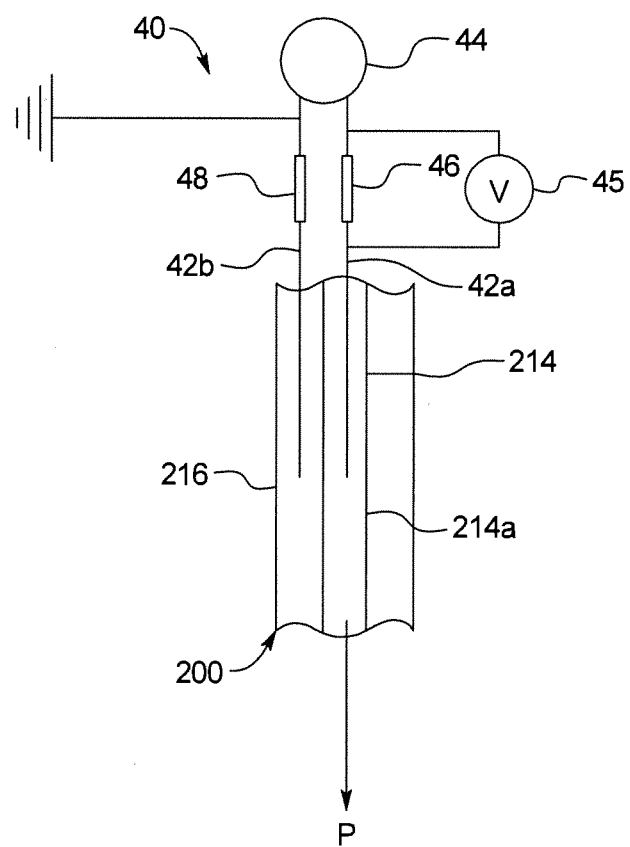
FIG. 2 is a schematic view of one embodiment of an electrode pair of the present disclosure.

In one embodiment shown in the sectioned view of FIG. 2, testing unit 20 is provided, at least in part, as a tubing assembly 200. The iodide and sample chamber or compartment 24 is a tube 214 disposed within a reducing agent chamber or compartment 26, which is also a tube 216, and which is of a larger diameter than that of tube 214 (chamber 24). In some embodiments, the outer reducing agent tube 216 has an inner diameter that is about 1.5 to about 4 times larger the outer diameter of the inner iodide and sample tube 214. Tube 214 (chamber 24) is in fluid communication with iodide reservoir 12 (not illustrated in FIG. 2), while tube 216 (chamber 26) is in fluid communication with reducing agent reservoir 14 (not illustrated in FIG. 2). The inner iodide and sample tube 214 includes or defines a plurality of perforations 214a, (membrane 28) e.g., hydrophobic perforations, which do not allow fluid to pass between chambers 24 and 26, but permit electrical conductivity to flow between the chambers (through the wall of narrower tube 214 into the outer diameter of larger tube 216).

The inner iodide and sample tube 214 is also in fluid communication with water to be tested (not illustrated in FIG. 2), which is pumped via line 52c and pump 18c from test sample outlet 58 of water purification machine 50. The tri-iodide generation loop of electrical circuit 40 includes electrodes 42a and 42b, each having or being in electrical communication with a respective resistor 46 and 48 (e.g., a 1 kΩ resistor). Electrode 42a of electrical circuit 40 is placed in contact with the fluid in the inner iodide and sample tube 214, while the other electrode 42b is placed in contact with the fluid in the outer reducing agent tube 216. In the illustrated embodiment, electrode 42b is grounded. As mentioned above, electrodes 42a and 42b can be formed of durable metal such as platinum, stainless steel, gold, copper, or be combinations or alloys thereof.

A voltage source 44 is provided (e.g., as part of electronics 40 or as part of control unit 60 or 110) to apply of a voltage, such as from about 0.7 VDC to about 1.0 VDC. The voltage source across the set resistance of resistors 46 and 48 generates a desired current. The applied current generates tri-iodide in the iodide and sample tube 214.

In one embodiment, control unit 60 or 110 causes the voltage to be applied for a period of time from about one minute to about ten minutes, for example about one minute, about two minutes, about three minutes, about four minutes, about five minutes, about six minutes, about seven minutes, about eight minutes, about nine minutes, or about ten minutes.

As discussed, in the illustrated embodiment, the electrical circuit 40 is also configured to measure voltage across membrane 28 or 214a. In an embodiment, when it is desired to measure the voltage across membrane 28 or 214a, control unit 60 or 110 causes the voltage from voltage source 44 used to generate tri-iodide to cease. Thereafter, control unit 60 or 110 causes the electrical circuit 40 to measure the voltage difference between the iodide and sample compartment 24 (tube 214) and the reducing agent chamber or compartment 26 (tube 216). In one embodiment, a voltage meter 45 measures the voltage across resistor 46.

In some embodiments, control unit 60 or 110 causes the voltage to be measured about once per second and anywhere in duration from about one minute to about 10 minutes, e.g., for example about 1 minute, about 2 minutes, about 3 minutes, about 4 minutes, about 5 minutes, about 6 minutes, about 7 minutes, about 8 minutes, about 9 minutes, or about 10 minutes. The measured voltage is proportional to the concentration of tri-iodide, which is in turn proportional to the amount of total chlorine in the water sample. In some embodiments, the measured voltage is a steady state voltage.

In one embodiment, iodide reservoir 12 is a chamber holding an iodide solution of known concentration, and which is in fluid communication with the iodide and sample chamber 24 as shown and discussed above. In some embodiments, iodide reservoir 12 holds about 0.1 gram to about one gram of iodide reagent (e.g., potassium iodide) in about one to about 10 mL of water. In some embodiments, the iodide reagent is a solution of about 0.25 gram to about 0.7 gram of iodide reagent in three to seven mL of water. In some embodiments, iodide reservoir 12 contains at least enough iodide reagent to last about one month or longer, e.g., from one month to six months, for example, so that refilling iodide reservoir 12 does not reduce the normal maintenance cycle of water purification unit 50. In some embodiments, the iodide reagent itself has a level of total chlorine that is below the detection limit for the system. In some embodiments, the iodide reagent has less than 0.1 ppm, less than 0.05 ppm, or less than 0.01 ppm of any total chlorine compound.

Reducing agent reservoir 14 is a chamber holding a reducing agent, such as a solution comprising a reducing agent. In some embodiments, the reducing agent reservoir includes about two to about twenty grams of a reducing agent (e.g., an alkaline sulfate such as sodium sulfate) in a suitable amount of water. In some embodiments, the reducing agent reservoir 14 holds about seventeen grams of reducing agent. In some embodiments, reducing agent reservoir 14 contains at least enough reducing agent to last about one month or longer, e.g., from one month to six months, for example, so that again refilling reducing agent reservoir 14 does not reduce the normal maintenance cycle of water purification unit 50.

In one preferred implementation, one mole of tri-iodide is generated for each mole of total chlorine. In some embodiments, the pump speeds of one or more or all of concentrate pumps 18a and 18b and test sample pump 18c are adjusted to optimize the ratio of moles of tri-iodide formed per moles of total chlorine in the water under test. In some embodiments, a higher pump speed generates closer to about one mole of tri-iodide per mole of total chlorine than a slower pump speed under otherwise identical conditions.

In some embodiments, chloramine-T is used as an artificial total chlorine source to optimize or calibrate pump speed based upon the measured current in the tri-iodide detection cell. In such an embodiment, a water sample with known total chlorine concentration may be prepared by combining a water sample with no or essentially no total chlorine content with a known amount of chloramine-T. The resulting water sample having a known total chlorine concentration may then be used to test the sensor, calibrate the system, or optimize pump speed.

In an embodiment, control unit 60 or 110 automatically performs multiple total chlorine determinations and averages the discrete results. It is also contemplated for system 10 to use an agitator, such as an ultrasonic vibrator, to agitate testing unit 20 during the test cycle to promote connectivity between the tri-iodide generation cell (chamber 24) and the tri-iodide detection cell (chambers 24 and 26). Other suitable mixing mechanisms include (but are not limited to): baffles, stirrers, agitators, vibration mechanisms, or any other suitable stirring mechanisms.

Figure 3:
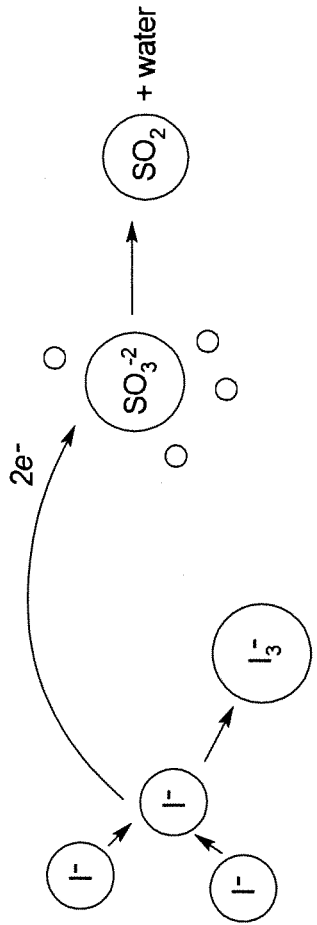
FIG. 3 is a schematic view of one representation of a mechanism in which a sodium sulfate anion promotes the conversion of three iodide anions to one tri-iodide anion and two electrons in water.
Figure 4:
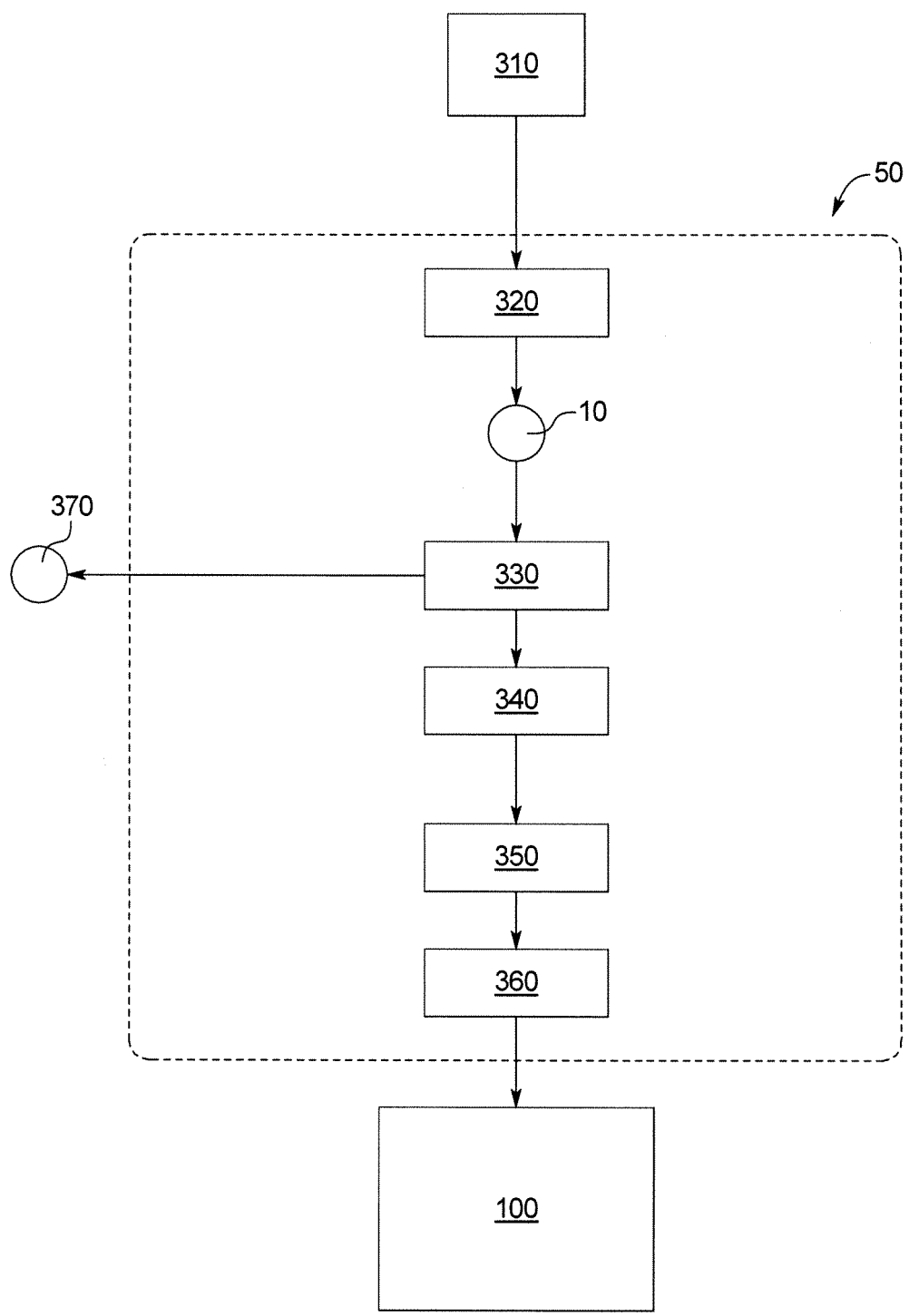
FIG. 4 is a schematic view of one embodiment of a water treatment system which includes a detection cell of the present disclosure.

FIG. 3 illustrates the principle of the electrochemical reaction. In aqueous solution, one equivalent of sulfate ($SO_4^{-2}$) promotes the conversion of three iodide anions ($I^-$) to one tri-iodide anion ($I_3^-$). The process consumes four equivalents of protons while producing one equivalent of $SO_2$ and one equivalent of water, and simultaneously liberating two electrons ($e^-$). When iodide anions are present in excess compared to the amount of total chlorine, the amount of tri-iodide produced is directly proportional to the amount of total chlorine present.

Example Methodology

In some embodiments, control unit 60 or 110 causes a process for determining an amount of total chlorine in the water under test to include:

(a) providing a total chlorine detection system as disclosed herein;

(b) providing a water sample, the water sample including an amount of total chlorine;

(c) measuring a background voltage $V_B$ in an electrode pair;

(d) metering an amount of the water sample into the system;

(e) monitoring a baseline voltage $V_0$ in the electrode pair, optionally for a time $t_0$, the baseline voltage $V_0$ associated with tri-iodide in the water sample, wherein the amount of tri-iodide in the water sample is associated with the amount of total chlorine in the water sample;

(f) generating a first amount of tri-iodide from the water sample by applying a voltage $V_1$ to the electrode pair for a time $t_1$;

(g) thereafter monitoring a first voltage $V_2$ in the electrode pair, optionally for a time $t_2$, the first voltage $V_2$ associated with the sum of the amount of total chlorine and the first amount of tri-iodide;

(h) thereafter generating a second amount of tri-iodide from the water sample by applying a voltage $V_3$ to the electrode pair for a time $t_3$;

(i) thereafter monitoring a second voltage $V_4$ in the electrode pair, optionally for a time $t_4$, the second voltage $V_4$ associated with the sum of the amount of total chlorine and the first and second amounts of generated tri-iodide;

(j) thereafter optionally generating a third amount of tri-iodide from the water sample by applying a voltage $V_5$ to the electrode pair for a time $t_5$;

(k) optionally monitoring a third voltage $V_6$ in the electrode pair for a time $t_6$, the third voltage $V_6$ associated with the sum of the amount of total chlorine and the first, second and third amounts of generated tri-iodide; and (l) calculating the amount of total chlorine in the water sample using at least one of the baseline voltage $V_0$, the first voltage $V_2$, the second voltage $V_4$, and the optional third voltage $V_6$, wherein each of the baseline voltage $V_0$, the first voltage $V_2$, the second voltage $V_4$, and the optional third voltage $V_6$ are corrected by first subtracting the background voltage $V_B$.

In some embodiments, the method also includes:

(m) repeating steps (g) to (k) to generate fourth, fifth, and sixth monitored voltages $V_8$, $V_{10}$ and $V_{12}$, respectively, before step (l); and (n) including the fourth, fifth, and sixth monitored voltages $V_8$, $V_{10}$ and $V_{12}$, respectively, in the calculation of step (l) after correcting for any background voltage $V_B$.

In some embodiments, the method further includes:

(o) repeating steps (g) to (h) an additional time to generate a seventh monitored voltage $V_{14}$ before step (l); and (p) including the seventh monitored voltage $V_{14}$ in the calculation of step (l) after correcting for any background voltage $V_B$.

The calculation step (l) can be accomplished using any suitable data analysis means based on one or more of the baseline voltage $V_0$ and first monitored voltage $V_2$, second monitored voltage $V_4$, optional third monitored voltage $V_6$, optional fourth monitored voltage $V_8$, optional fifth monitored voltage $V_{10}$, optional sixth monitored voltage $V_{12}$, and optional seventh monitored voltage $V_{14}$. In an example methodology, calculating the total chlorine concentration in the water sample in step (l) above includes:

(i) plotting the plurality of monitored voltage values (e.g., $V_2$, $V_4$, $V_6$, $V_8$, $V_{10}$, $V_{12}$, etc.) (y-axis), optionally corrected for any background voltage $V_B$, as a function of relative tri-iodide concentration, wherein the first relative tri-iodide concentration is set to x=0; and (ii) extrapolating a line of best fit using at least two of the plurality of monitored voltage values $V_2$, $V_4$, $V_6$, etc., optionally corrected for any background voltage $V_B$, to a point where y is equal to the baseline voltage $V_0$ and correlating that point to determine the x-value ("$x_0$") associated with said point, wherein the unknown total chlorine concentration is equal to $(-1)(x_0)$.

In any embodiment described herein, the monitored voltages $V_0$, $V_2$, $V_4$, $V_6$, $V_8$, $V_{10}$, $V_{12}$, etc., can be corrected to exclude any background tri-iodide present in the system by subtracting the background voltage $V_B$ from each monitored voltage value. In other embodiments, background tri-iodide present in, for example, the iodide reagent, can be reduced, minimized or eliminated by reversing the polarity of the tri-iodide generation electrode and applying a suitable voltage for a period of time sufficient to convert any background tri-iodide to iodide before introduction of a water sample.

In some embodiments, the applied voltages $V_1$, $V_3$, $V_5$, $V_7$, etc. are all the same or substantially the same.

In some embodiments, control unit 60 or 110 causes tri-iodide generating times $t_1$, $t_3$, $t_5$, $t_7$, $t_9$, . . . , to be substantially the same, essentially the same, or the same. In some embodiments, control unit 60 or 110 causes tri-iodide generating times $t_1$, $t_3$, $t_5$, $t_7$, $t_9$, . . . , to each be about one minute to about ten minutes, for example about one minute, about two minutes, about three minutes, about four minutes, about five minutes, about six minutes, about seven minutes, about eight minutes, about nine minutes, or about ten minutes. In some embodiments, tri-iodide generating times $t_1$, $t_3$, $t_5$, $t_7$, $t_9$, . . . , are each about five minutes.

In some embodiments, control unit 60 or 110 causes voltage monitoring times $t_2$, $t_4$, $t_6$, $t_8$, $t_{10}$, . . . , to be substantially the same, essentially the same, or the same. In some embodiments, control unit 60 or 110 causes voltage monitoring times $t_2, t_4, t_6, t_8, t_{10}, \ldots$, to each be about one minute to about ten minutes, for example about one minute, about two minutes, about three minutes, about four minutes, about five minutes, about six minutes, about seven minutes, about eight minutes, about nine minutes, or about ten minutes. In some embodiments, control unit 60 or 110 causes voltage monitoring times $t_2, t_4, t_6, t_8, t_{10}, \ldots$, to each be about five minutes.

In some embodiments, control unit 60 or 110 causes the voltage to be monitored by measuring the voltage a single time. In alternative embodiments, control unit 60 or 110 causes the voltage to be monitored by measuring a voltage at a rate of about one measurement per ten seconds (e.g., 0.1 Hz) to about ten measurements per second (e.g., 10 Hz), for example about 0.1 Hz, about 0.2 Hz, about 0.3 Hz, about 0.4 Hz, about 0.5 Hz, about 0.6 Hz, about 0.7 Hz, about 0.8 Hz, about 0.9 Hz, about 1 Hz, about 2 Hz, about 3 Hz, about 4 Hz, about 5 Hz, about 6 Hz, about 7 Hz, about 8 Hz, about 9 Hz, or about 10 Hz. In some embodiments, the voltage is measured a plurality of times during the measurement time period, for example about five times, about six times, about seven times, about eight times, about nine times, about ten times, about fifteen times, about twenty times, about thirty times, about forty times, about fifty times, about sixty times, about seventy times, about eighty times, about ninety times, about 100 times, about 150 times, about 200 times, about 250 times, about 300 times, about 350 times, about 360 times, about 400 times, about 450 times, about 500 times, about 550 times, about 600 times, about 650 times, about 700 times, about 750 times, about 800 times, about 850 times, about 900 times, about 950 times, about 1000 times, about 1200 times, about 1500 times, about 1800 times, about 2000 times, about 2400 times, about 2500 times, about 3000 times, about 3500 times, about 3600 times, about 4000 times, about 4200 times, about 4500 times, about 4800 times, about 5000 times, about 5400 times, about 5500 times, or about 6000 times during the voltage measurement time period.

In some embodiments, control unit 60 or 110 causes the voltage to be measured one time per second over the course of one minute.

In some embodiments, control unit 60 or 110 causes an amount of time between a voltage monitoring step (e.g., any one of steps (f), (h), (j), etc.) and a subsequent tri-iodide generation step (e.g., any one of steps (g), (i), (k), etc.) to be sufficient to allow the tri-iodide and/or the voltage to equilibrate. In some embodiments, control unit 60 or 110 causes the amount of time is about one minute to about ten minutes, for example about one minute, about two minutes, about three minutes, about four minutes, about five minutes, about six minutes, about seven minutes, about eight minutes, about nine minutes, or about ten minutes. In some embodiments, an amount of time between steps (d) and (e) is no less than about one minute, about two minutes, about three minutes, about four minutes, about five minutes, about six minutes, about seven minutes, about eight minutes, about nine minutes, or about ten minutes.

In some embodiments, control unit 60 or 110 causes the amount of time between a tri-iodide generating step (e.g., any one of steps (e), (g), (i), etc.) and a subsequent voltage monitoring step (e.g., any one of steps (f), (h), (j), etc.) is sufficient to allow the tri-iodide and/or the voltage to equilibrate. In some embodiments, the amount of time is about ten seconds to about five minutes, for example about ten seconds, about fifteen seconds, about twenty seconds, about thirty seconds, about forty seconds, about forty-five seconds, about fifty seconds, about one minute, about 1.25 minutes, about 1.5 minutes, about 1.75 minutes, about two minutes, about 2.25 minutes, about 2.5 minutes, about 2.75 minutes, about three minutes, about 3.25 minutes, about 3.5 minutes, about 3.75 minutes, about four minutes, about 4.25 minutes, about 4.5 minutes, about 4.75 minutes, or about five minutes.

Example Method of Calculation

Control unit 60 or 110 can be programmed to perform the following calculations.

Calculation 1. Average the last thirty readings of each period following a chlorine addition or electrochemical generation of iodide.

Calculation 2. Compute the average change in voltage with tri-iodide concentration by plotting the change in measured voltage (y-axis) between successive periods of tri-iodide generation (x-axis). Use measured current to compute the amount of tri-iodide ($[I_3^-]$) generated as:

$$[I_3^-] = i * t / 2F * V,$$

where i=current (A or charge/s), t=time (s), F=Faraday's constant (charge/mole of electrons), V=iodide reagent solution volume (L), and 2 represents the number of electrons transferred between iodide and tri-iodide.

Calculation 3. Divide difference of the voltage measured before the addition of total chlorine and the voltage measured after the addition of chlorine by the computed slope to calculate the tri-iodide concentration of the water sample.

Example Operation

Step 1. Add 0.25 gram to 0.7 gram of KI and 3 mL to 7 mL of water to the KI reservoir, and two grams to twenty grams of $Na_2SO_4$ and 225 mL water to the $Na_2SO_4$ reservoir.

Step 2. 200 µL of water under test are then pumped via, e.g., a microfluidic pump, into the KI and water sample chamber 24 of the main unit.

Step 3. 700 mV is then applied to electrode pair 42a and 42b to generate tri-iodide. Optionally, the main unit is agitated to promote mass transfer.

Step 4. The voltage across electrode pair 42a and 42b is then measured.

Step 5. Steps 2 to 4 are repeated twice to ten times.

Step 6. Lines 52d, 52e and 52f are then opened and the main unit is flushed with DI water.

Step 7. The voltage values recorded in each iteration of Step 4 are used in comparison to calibration data derived from testing system 10 with known amounts of total chlorine to calculate a level of total chlorine in the water under test. This result can be displayed on a display device (e.g., a display device or tablet 112 of dialysis machine 100 or display device 62 of water purification machine 50). Alternatively or additionally, an indicator (such as an audible alarm and/or a visual alarm) can be used to notify a user when the amount of total chlorine in the water under test is above (or below) a predetermined threshold (e.g., 0.1 ppm).

Water Purification and Dialysis Machine Configuration Using the Total Chlorine Detection System As discussed herein, water purification machine 50 can house or operate with the chlorine sensing system 10 of the present disclosure. To that end, chlorine sensing in system 10 may be in fluid connection with water purification machine 50 at any suitable location along the fluid path of the machine.

Referring now generally to FIGS. 4 to 7, in one embodiment, water purification machine 50 is in fluid connection with a water source 310. Water source 310 may be any water source suitable for home use including, for example, a municipal water source or a well water source. In the illustrated embodiment, water purification machine 50 includes a water pretreatment filter 320, which may include any number of filters and/or sorbents for removing impurities from the water obtained from the water source 310. In some embodiments, the water pretreatment filter 320 includes a carbon filter. In the embodiment shown in FIG. 4, water pretreatment filter 320 is in fluid connection with chlorine sensing system 10 as described herein. In this embodiment, chlorine sensing system 10 is also in fluid connection with a reverse osmosis filter 330. The reverse osmosis filter 330 is in turn in fluid connection with a drain 370 and an electrodeionization ("EDI") module 340, which may optionally further include an electrodialysis component. The EDI module 340 is in fluid connection with an ultraviolet lamp or filter 350, which in turn is in fluid connection with a bacterial filter 360. Bacterial filter 360 may optionally further include an endotoxin filter. Water treated by water purification machine 50 may be used with a downstream dialysis machine 100, such as a hemodialysis system or home hemodialysis machine as has been described herein.

Figure 5:
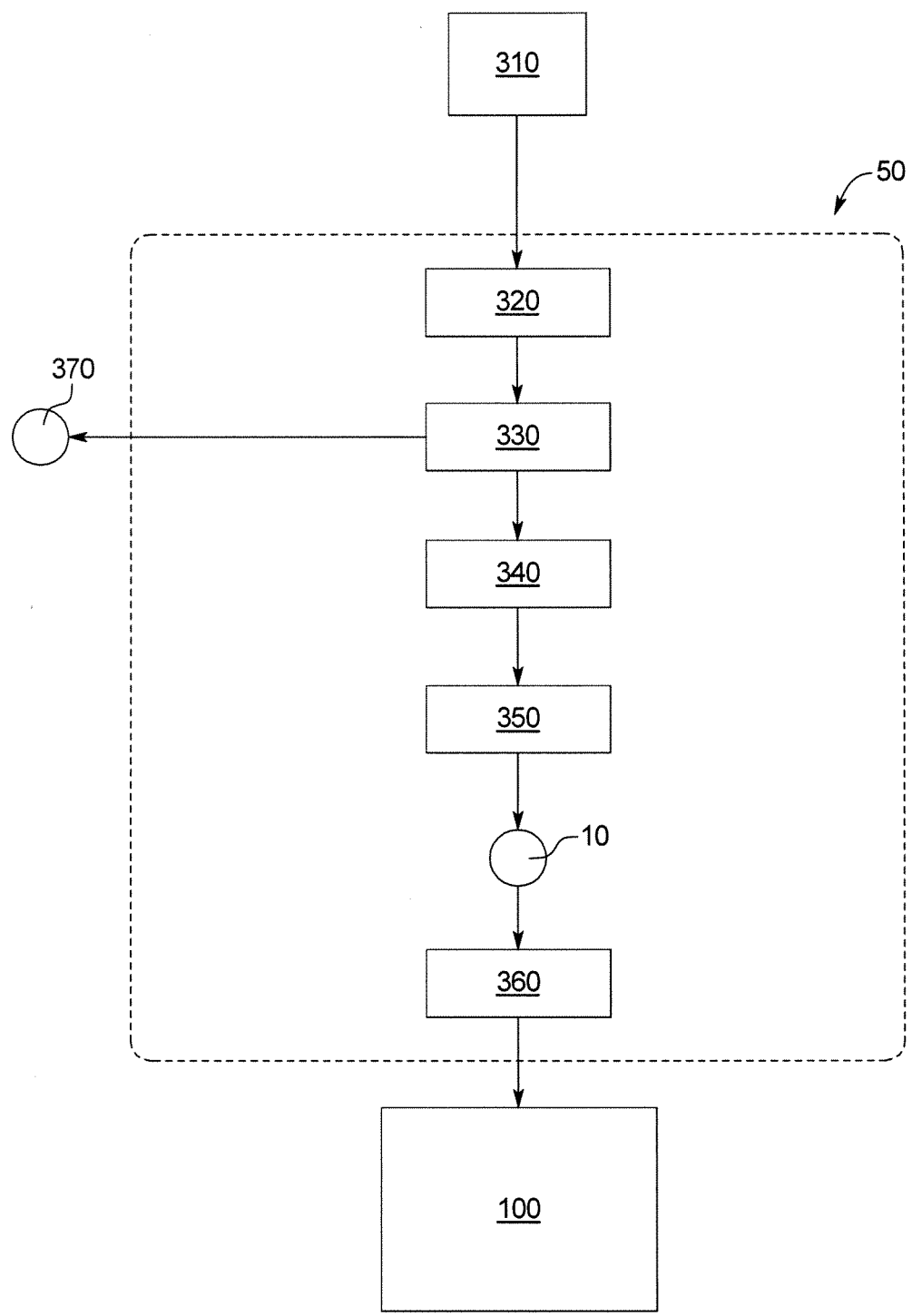
FIG. 5 is a schematic view of one embodiment of a water treatment system which includes a detection cell of the present disclosure.
Figure 6:
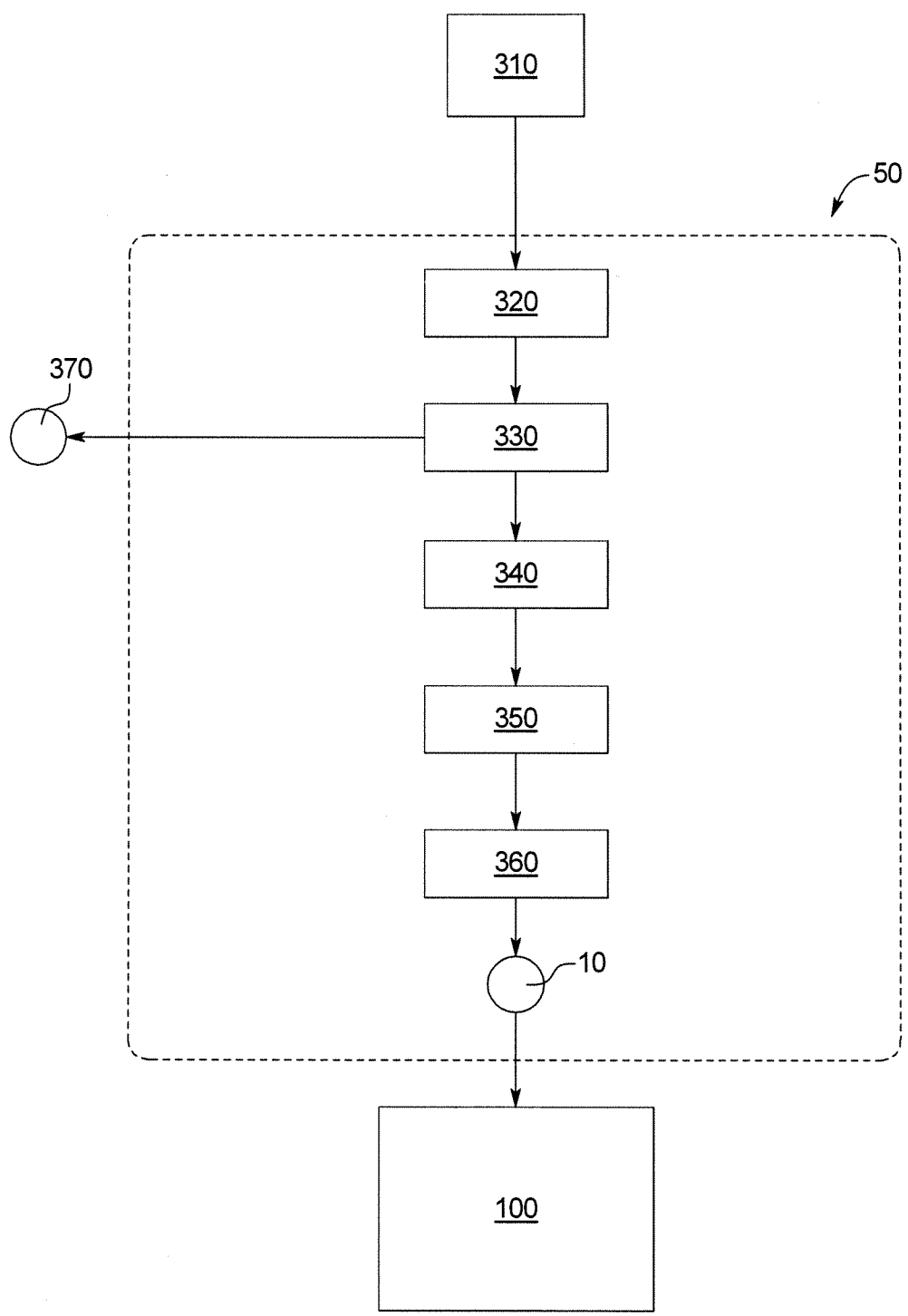
FIG. 6 is a schematic view of one embodiment of a water treatment system which includes a detection cell of the present disclosure.

As illustrated in FIGS. 5 to 7, chlorine sensing system 10 may alternatively be in fluid connection with the ultraviolet lamp or filter 350 and the bacterial filter 360 (FIG. 5); with the bacterial filter 360 and dialysis machine 100 (FIG. 6); or with the water source 310 and the water pretreatment filter 320 (FIG. 7). In some embodiments, the chlorine sensing system 10 is in fluid connection with the water pathway of the water purification machine 50 via a sampling port (not shown).

Aspects of the Present Disclosure

Aspects of the subject matter described herein may be useful alone or in combination with one or more other aspect described herein. Without limiting the foregoing description, in a first aspect of the present disclosure, a system for determining a level of total chlorine in a dialysis water sample, the system includes (i) a water purification machine, (ii) a dialysis machine in fluid communication with the water purification machine, and (iii) a total chlorine detector in fluid communication with the water purification machine, said total chlorine detector including (a) an iodide reservoir, (b) a reducing agent reservoir, (c) a first chamber in fluid communication with the iodide reservoir and a water sample produced by the water purification machine, (d) a second chamber in fluid communication with the reducing agent reservoir, wherein the first and second chambers are separated by a membrane that allows charge but not fluid to pass between the chambers, (e) an electrode pair associated with a voltage source, wherein one electrode of the electrode pair is in contact with iodide fluid and the water sample mixed in the first chamber and the other electrode of the electrode pair is in contact with a reducing agent solution in the second chamber, and (f) a control unit connected operably to the electrode pair, the control unit configured to (1) at one time cause the voltage source to apply a source voltage to the electrode pair and (2) at a second time stop applying the source voltage to the electrode pair and instead monitor a sensed electrical parameter through or across the electrode pair.

In accordance with a second aspect of the present disclosure, which can be used in combination with any other aspect or aspects listed herein, at least one of the electrodes includes platinum, gold, stainless steel, copper, combinations or alloys thereof.

In accordance with a third aspect of the present disclosure, which can be used in combination with any other aspect or aspects listed herein, at least one of the first and second chambers includes a tube.

In accordance with a fourth aspect of the present disclosure, which can be used in combination with any other aspect or aspects listed herein, the first and second chambers both include tubes, and wherein the first chamber is disposed within a lumen of the second tube.

In accordance with a fifth aspect of the present disclosure, which can be used with the second aspect in combination with any other aspect or aspects listed herein, the membrane is selected from the group consisting of: a semipermeable membrane, and a membrane including a plurality of perforations.

In accordance with a sixth aspect of the present disclosure, which can be used in combination with any other aspect or aspects listed herein, at least one electrode of the electrode pair includes or is provided with a resistor.

In accordance with a seventh aspect of the present disclosure, which can be used in combination with any other aspect or aspects listed herein, one electrode of the electrode pair is placed in electrical communication with a ground.

In accordance with an eighth aspect of the present disclosure, which can be used in combination with any other aspect or aspects listed herein, the system includes an agitator in contact with at least one of the first and second chambers.

In accordance with a ninth aspect of the present disclosure, which can be used in combination with any other aspect or aspects listed herein, tri-iodide is generated when the control unit causes the voltage source to apply a source voltage to the electrode pair.

In accordance with a tenth aspect of the present disclosure, which can be used in combination with any other aspect or aspects listed herein, the control unit can determine an amount of total chlorine in the water sample when the control unit stops applying source voltage to the electrode pair and instead monitors a sensed electrical parameter through or across the electrode pair.

In accordance with an eleventh aspect of the present disclosure, which can be used in combination with any other aspect or aspects listed herein, the control unit is configured to sequentially (1) at one time cause the voltage source to apply a source voltage to the electrode pair and (2) at a second time stop applying the source voltage to the electrode pair and instead monitor a sensed electrical parameter through or across the electrode pair multiple times.

In accordance with a twelfth aspect of the present disclosure, which can be used with the eleventh aspect in combination with any other aspect or aspects listed herein, the control unit is further configured to merge results obtained from performing (1) at one time cause the voltage source to apply a source voltage to the electrode pair and (2) at a second time stop applying the source voltage to the electrode pair and instead monitor a sensed electrical parameter through or across the electrode pair multiple times.

In accordance with a thirteenth aspect of the present disclosure, which can be used with any other aspect or aspects listed herein, the system is embedded into the water purification machine enabling at least one filter of the water purification machine to be evaluated.

In accordance with a fourteenth aspect of the present disclosure, which can be used in combination with any other aspect or aspects listed herein, the total chlorine detector is downstream of a water filter including carbon.

In accordance with a fifteenth aspect of the present disclosure, which can be used in combination with any other aspect or aspects listed herein, the system includes a user interface configured and arranged to indicate at least one of (a) an alarm to a user if a level of total chlorine in the water sample exceeds a predetermined value or (b) indicate a safe status to a user if the level of total chlorine in the water sample falls below a predetermined value.

In accordance with a sixteenth aspect of the present disclosure, which can be used with the fifteenth aspect in combination with any other aspect or aspects listed herein, the predetermined value of total chlorine is between and including 0.1 ppm to 0.5 ppm.

In accordance with a seventeenth aspect of the present disclosure, which can be used in combination with any other aspect or aspects listed herein, at least one of the first chamber, the iodide reservoir, or the reducing agent reservoir is provided in a replaceable cartridge or cassette form.

In accordance with an eighteenth aspect of the present disclosure, which can be used in combination with any other aspect or aspects listed herein, the system includes a plurality of pumps and valves positioned and arranged to meter preset amounts of sample water and iodide reagent into the first chamber and reducing agent into the second chamber.

In accordance with a nineteenth aspect of the present disclosure, which can be used in combination with any other aspect or aspects listed herein, the system includes at least one pump and valve positioned and arranged to pump deionized water into at least one of the first and second chambers.

In accordance with a twentieth aspect of the present disclosure, which can be used in combination with any other aspect or aspects listed herein, the system includes at least one pump and valve positioned and arranged to pull fluid from at least one of the first and second chambers to drain.

In accordance with a twenty-first aspect of the present disclosure, which can be used in combination with any other aspect or aspects listed herein, the system is provided as part of the water purification machine feeding water to the dialysis machine that prepares dialysate using the water from the water purification machine, and wherein information concerning the level total chlorine is displayed on a user interface of the dialysis machine.

In accordance with a twenty-second aspect of the present disclosure, which can be used in combination with any other aspect or aspects listed herein, a method of providing a hemodialysis treatment to a subject in need thereof, the method includes (i) providing a system as described herein, wherein the water sample is from water for preparing dialysate, and (ii) determining a level of total chlorine in the water sample, (iii) alerting the user to perform a corrective action if the level of total chlorine exceeds a predetermined level, and (iv) allowing the user to perform the hemodialysis treatment if the level of total chlorine is below the predetermined level.

In accordance with a twenty-third aspect of the present disclosure, which can be used with the twenty-second aspect in combination with any other aspect or aspects listed herein, an alerting step further includes preventing the user from performing the hemodialysis treatment until a subsequent level of total chlorine in a subsequent water sample is below the predetermined level.

In accordance with a twenty-fourth aspect of the present disclosure, which can be used with the twenty-second aspect in combination with any other aspect or aspects listed herein, a water sample is from water for preparing dialysate that has been passed through a filter including carbon.

In accordance with a twenty-fifth aspect of the present disclosure, which can be used in combination with any other aspect or aspects listed herein, a method of for determining an amount of total chlorine in water for dialysis, the method includes (i) providing a water purification machine in fluid communication with a dialysis machine, (ii) providing a total chlorine detection system, in fluid communication with the water purification machine, the total chlorine detection system including a first chamber in fluid communication with an iodide reservoir and a water sample source, a second chamber in fluid communication with a reducing agent reservoir, and an electrode pair associated with a voltage source, wherein one electrode of the electrode pair is in contact with an iodide fluid in the first chamber and the other electrode of the electrode pair is in contact with a reducing agent solution in the second chamber, and wherein the first and second chambers are separated by a membrane that allows charge but not fluid to pass between the chambers, (iii) providing the water sample, the water sample including an amount of total chlorine, (iv) measuring a background voltage $V_B$ in the electrode pair, the background voltage $V_B$ associated with any tri-iodide present in the system before introduction of the water sample, (v) metering an amount of the water sample into the system, (vi) monitoring a baseline voltage $V_0$ via the electrode pair, the baseline voltage $V_0$ associated with system after the at least partially purified water sample is provided by the water purification machine but before tri-iodide is generated by applying a voltage to the electrode pair, (vii) generating a first amount of tri-iodide from the water sample by applying a voltage $V_1$ to the electrode pair for a time $t_1$, (viii) thereafter monitoring a first voltage $V_2$ in the electrode pair, optionally for a time $t_2$, the first monitored voltage $V_2$ associated with the sum of the amount of total chlorine and the first amount of generated tri-iodide, (ix) thereafter generating a second amount of tri-iodide from the water sample by applying a voltage $V_3$ to the electrode pair for a time $t_3$, (x) thereafter monitoring a second voltage $V_4$ in the electrode pair, optionally for a time $t_4$, the second monitored voltage $V_4$ associated with the sum of the amount of total chlorine and the first and second amounts of generated tri-iodide, (xi) thereafter optionally generating a third amount of tri-iodide from the water sample by applying a voltage $V_5$ to the electrode pair for a time $t_5$, the third amount of tri-iodide corresponding to the third amount of tri-iodide, (xii) optionally monitoring a third voltage $V_6$ in the electrode pair, optionally for a time $t_6$, the third monitored voltage $V_6$ associated with the sum of the amount of total chlorine and the first, second and third amounts of generated tri-iodide, and (xiii) calculating the amount of total chlorine in the water sample from the baseline voltage $V_0$, the background voltage $V_B$, and at least one of the first, second and optional third monitored voltages $V_2$, $V_4$ and $V_6$.

In accordance with a twenty-sixth aspect of the present disclosure, any of the structure and functionality illustrated or described in connection with FIGS. 1 to 7 can be used in combination with any other aspect or aspects listed herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A chlorine detector comprising:
    a first chamber in fluid communication with an iodide reservoir and a source of at least partially purified water;
    a second chamber in fluid communication with a reducing agent reservoir, wherein the first and second chambers are separated by a membrane that allows an electrical charge but not fluid to pass between the chambers;
    an electrode pair associated with a voltage source, wherein one electrode of the electrode pair is in contact with an interior of the first chamber and the other electrode of the electrode pair is in contact with an interior of the second chamber; and
    a control unit connected operably to the electrode pair, the control unit configured to (i) at one time cause the voltage source to apply a source voltage to the electrode pair and (ii) at a second time stop applying the source voltage to the electrode pair and instead monitor an electrical parameter through or across the electrode pair.

2. The chlorine detector of claim 1, wherein at least one of the electrodes includes a metal selected from the group consisting of platinum, gold, stainless steel, copper, combinations thereof, and alloys thereof.

3. The chlorine detector of claim 1, wherein at least one of the first and second chambers includes a tube.

4. The chlorine detector of claim 1, wherein the first and second chambers both include tubes, and wherein the first chamber is disposed within a lumen of the second tube.

5. The chlorine detector of claim 1, wherein at least one electrode of the electrode pair comprises a resistor.

6. The chlorine detector of claim 1, wherein one electrode of the electrode pair is placed in electrical communication with a ground.

7. The chlorine detector of claim 1 comprising an agitator in contact with at least one of the first and second chambers.

8. The chlorine detector of claim 1, wherein at least one of the first chamber, the iodide reservoir, or the reducing agent reservoir is in a replaceable cartridge or cassette form.

9. The chlorine detector of claim 1 comprising at least one pump and valve configured to pump deionized water into at least one of the first and second chambers.

10. The chlorine detector of claim 1 comprising at least one pump and valve configured to pull fluid from at least one of the first and second chambers to drain.

* * * * *